United States Patent [19]

Ito et al.

[11] Patent Number: 5,172,418
[45] Date of Patent: Dec. 15, 1992

[54] IMAGE PROCESSING APPARATUS USING DISEASE-BASED IMAGE PROCESSING CONDITIONS

[75] Inventors: Wataru Ito; Nobuyoshi Nakajima, both of Kanagawa, Japan

[73] Assignee: Fuji Photo Film Co., Ltd., Kanagawa, Japan

[21] Appl. No.: 564,238

[22] Filed: Aug. 8, 1990

[30] Foreign Application Priority Data

Aug. 10, 1989 [JP] Japan .................. 1-207353
Apr. 18, 1990 [JP] Japan .................. 2-102022

[51] Int. Cl.⁵ .................. G06K 9/00; G06K 9/40; G06F 15/00
[52] U.S. Cl. .................. 382/6; 382/54; 364/413.13
[58] Field of Search .................. 382/6, 54; 364/413.13, 364/413.14, 413.15

[56] References Cited

U.S. PATENT DOCUMENTS

| | | | |
|---|---|---|---|
| 4,199,748 | 4/1980 | Bacus | 382/6 |
| 4,232,970 | 11/1980 | Sawamura et al. | 382/6 |
| 4,258,264 | 3/1981 | Kotera et al. | 250/484 |
| 4,276,473 | 6/1981 | Kato et al. | 250/327 |
| 4,315,318 | 2/1982 | Kato et al. | 382/54 |
| 4,387,428 | 6/1983 | Ishida et al. | 364/414 |
| 4,430,749 | 2/1984 | Schardt | 382/6 |
| 4,453,266 | 6/1984 | Bacus | 382/6 |
| 4,563,701 | 1/1986 | Gilath et al. | 364/413.13 |
| 4,764,870 | 8/1988 | Haskin | 364/413.13 |
| 4,920,491 | 4/1990 | Eberhard et al. | 382/6 |
| 4,945,478 | 7/1990 | Merickel et al. | 382/6 |
| 4,995,093 | 2/1991 | Funahashi et al. | 382/6 |
| 4,998,284 | 3/1991 | Bacus | 382/6 |

Primary Examiner—Michael T. Razavi
Assistant Examiner—Michael R. Cammarata
Attorney, Agent, or Firm—Sughrue, Mion, Zinn, Macpeak & Seas

[57] ABSTRACT

An image processing apparatus processes diagnostic image data bearing thereon an image through which a disease is to be diagnosed so that a visible image having a quality optimal to diagnose the disease can be obtained. The image processing apparatus includes an image processing condition storage section and an image processing section. Names of various diseases and image processing conditions for the respective diseases are stored in the image processing condition storage section. The diagnostic image data is input into the image processing section. The name of a disease which is to be diagnosed is input into the image processing condition storage section, and the image processing condition corresponding to the disease is input into the image processing section from the image processing condition storage section. The image processing section carries out image processing on the image data according to the image processing condition input thereinto and generates a processed image data. The processed image data is sent to an image reproducing system where a visible image is reproduced on the basis of the processed image data.

4 Claims, 5 Drawing Sheets

IMAGE PROCESSING APPARATUS USING DISEASE-BASED IMAGE PROCESSING CONDITIONS

BACKGROUND OF THE INVENTION

1. Field of the Invention

This invention relates to an image processing apparatus for processing an image signal representing a diagnostic image in order to obtain a visible image suitable for diagnosis.

2. Description of the Prior Art

Techniques for reading out a recorded radiation image in order to obtain an image signal, carrying out appropriate image processing on the image signal, and then reproducing a visible image by use of the processed image signal have heretofore been known in various fields. For example, an X-ray image is recorded on an X-ray film having a small gamma value chosen according to the type of image processing to be carried out, the X-ray image is read out from the X-ray film and converted into an electric signal (image signal), and the image signal is processed and then used for reproducing the X-ray image as a visible image on a copy photograph or the like. In this manner, a visible image having good image quality with high contrast, high sharpness, high graininess, or the like can be reproduced.

Also, when certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object such as the human body in order to store a radiation image of the object thereon, and is then scanned with stimulating rays, such as a laser beam, which cause it to emit light in proportion to the amount of energy stored during exposure to the radiation. The light emitted by the stimulable phosphor sheet, upon stimulation thereof, is photoelectrically detected and converted into an electric image signal- The image signal is then used to reproduce the radiation image of the object as a visible image on a recording material such as photographic film, on a display device such as a cathode ray tube (CRT), or the like.

Radiation image recording and reproducing systems which use stimulable phosphor sheets are advantageous over conventional radiography using silver halide photographic materials, in that images can be recorded even when the energy intensity of the radiation to which the stimulable phosphor sheet is exposed varies over a wide range. More specifically, since the amount of light which the stimulable phosphor sheet emits when being stimulated varies over a wide range and is proportional to the amount of energy stored thereon during its exposure to the radiation, it is possible to obtain an image having a desirable density regardless of the energy intensity of the radiation to which the stimulable phosphor sheet was exposed. In order to obtain the desired image density, an appropriate read-out gain is set when the emitted light is being detected and converted into an electric signal to be used in the reproduction of a visible image on a recording material, such as photographic film, or on a display device, such as a CRT. This system is especially preferable to obtain a diagnostic image where reduction of radiation dose is required.

In the aforesaid systems, various image processings are carried out on the image signal in order to obtain a visible image suitable for diagnostic purposes as disclosed, for instance in Japanese Unexamined Patent Publication No. 55(1980)-87983, U.S. Pat. No. 4,315,318, and U.S. patent application No. 259,814.

However when the image processing methods which have been proposed are applied to an actual image, it must be determined what spatial frequency is to be enhanced (or weakened) to what extent, and the like. In the systems which treats a large number of images, it is very troublesome and inefficient to determine the image processing condition for each image by trial and error. Accordingly, there has been commonly used a method in which the images are grouped and the image processing condition is determined in advance for each group. For example, in the systems for treating diagnostic images, the images are generally grouped by the recorded parts (e.g., head, neck, chest and abdomen) and/or the recording conditions (normal radiography, tomography and enlarged radiography).

For example, in the case of an image of the chest, the doctor sometimes wants to inspect the heart and sometimes wants to inspect the lung, and accordingly, the image processing condition has been determined so that a visible image having acceptable image quality over the entire chest can be reproduced. However this means that neither of the image of the heart nor the image of the lung has the best image quality.

SUMMARY OF THE INVENTION

In view of the foregoing observations and description, the primary object of the present invention is to provide an image processing apparatus in which the image signal of areas which interest doctors can be processed optimally with a higher probability.

As shown in FIG. 1, the image processing apparatus in accordance with the present invention comprises an image processing condition storage section 1 and an image processing section 2. Names of various diseases and image processing conditions for the respective diseases are stored in the image processing condition storage section 1.

A diagnostic image data Sl which is to be processed is input into the image processing section 2. Simultaneously with input of the image data S1 to the image processing section 2 or immediately before or after it, the name of a disease D which is to be diagnosed on the basis of the diagnostic image carried by the image data S1 is input into the image processing condition storage section 1, and the image processing condition P corresponding to the disease is input into the image processing section 2 from the image processing condition storage section 1. The image processing section 2 carries out image processing on the image data S1 according to the image processing condition P input thereinto and generates a processed image data S2. The processed image data S2 is sent to an image reproducing system (not shown) where a visible image is reproduced on the basis of the processed image data S2 or sent to an image storage system to be reproduced later.

The name of the disease D may be manually input for each diagnostic image, but it is preferred that the name of the disease D be automatically determined according to the clinical history of the patient, the results of medical tests and the like, and the image data be processed according to the image processing condition corresponding to the name of the disease thus determined.

That is, in a preferred embodiment of the present invention, a data analyzing section 3 and a diagnosis knowledge base storage section 4 are added as shown in FIG. 2.

Into the data analyzing section 3 is input patient information I. The patient information I includes various data on the patient corresponding to the image data S1 which is input or has been input into the image processing section 2, e.g., age, physical features of the patient such as sex, results of various medical tests such as blood test and urinalysis, degree of drinking and/or smoking, business career, patient's own clinical history, clinical history of the patient's family, and the like.

In the diagnosis knowledge base storage section 4 is stored in advance a diagnosis knowledge base for relating one or more of the data included in the patient information I to the probability of various diseases to be diagnosed. For example, when the patient information says that the patient has been a coal miner for not less than fifteen years, it is determined that there is a high probability that he is suffering from pneumoconiosis, or when the patient information says that it is within a predetermined time since the patient was operated on for cancer, it is determined that there is a high probability that he is suffering from the cancer.

In the data analyzing section 3, one or more probable diseases are specified with reference to the diagnosis knowledge base stored in the diagnosis knowledge base storage section 4, and the names of the diseases are delivered to the image processing condition storage section 1. Then, as in the image processing apparatus shown in FIG. 1, the image processing condition P corresponding to the disease is input into the image processing section 2 from the image processing condition storage section 1. The image processing section 2 carries out image processing on the image data S1 according to the image processing condition P input thereinto and generates a processed image data S2.

As shown by the broken line in FIG. 2, the apparatus may be so arranged that the image data S1 is input into the data analyzing section 3 together with the patient information I, the image data S1 is searched for an image of abnormality which is useful for specifying the disease such as an image corresponding to cancer, an image corresponding to pneumoconiosis, or the like (See, for instance, Japanese Unexamined Patent Publication No. 62(1987)-125481 and Japanese Patent Application Nos. 1(1989)-162901 to 162909), and the name of disease corresponding to the image of abnormality, if found, is delivered to the image processing condition storage section 1.

Names of more than one diseases may be input into the image processing condition storage section 1 in either of the image processing apparatuses shown in FIGS. 1 and 2 and the image processing condition storage section 1 may output a plurality of image processing conditions P which are suitable for the respective names of diseases. In such a case, the image processing section 2 carries out image processing on the image data S1 a plurality of times according to the respective image processing conditions P and generates a plurality of processed image data S2.

In the image processing apparatus in accordance with the present invention, the image processing conditions and the names of diseases are related to each other and are stored, and the image data is processed according to the image processing condition corresponding to the name of disease to be diagnosed. Accordingly, compared with the conventional image processing apparatus where the image processing condition is determined on the basis of the recorded parts, the areas which interest doctors can be processed optimally with a higher probability.

The name of disease may be manually input for each diagnostic image. However, in some cases, the disease cannot be diagnosed until the image is viewed. In such cases, the image is once reproduced and the disease is diagnosed roughly. Then the name of disease is input and the image data is processed according to the image processing condition corresponding to the name of disease. Then a visible image is reproduced again on the basis of the optimally processed image data.

On the other hand, in the preferred embodiment of the present invention, the name of disease is automatically determined on the basis of the patient information and accordingly, the time required to obtain an optimally processed image can be reduced and trouble to doctors or the like is reduced.

DESCRIPTION OF THE PREFERRED EMBODIMENT

Figure 3:
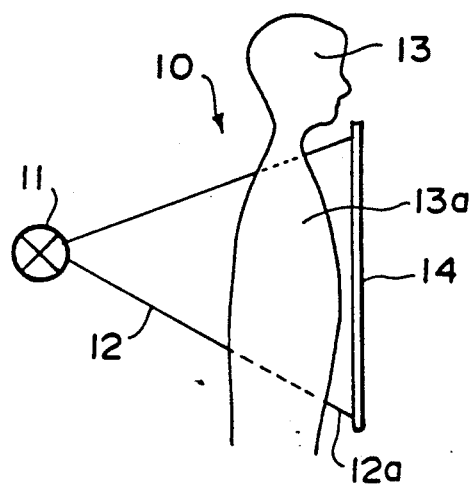
FIG. 3 is a schematic view showing an example of an X-ray image recording apparatus.

In FIG. 3, an X-ray image recording apparatus 10 includes an X-ray source 11. X-rays 12 are projected from the X-ray source 11 toward the chest 13a of a human body 13 and a stimulable phosphor sheet 14 is exposed to X-rays 12a which has passed through the human body 13 and stores an X-ray image of the chest 13a.

Figure 4:
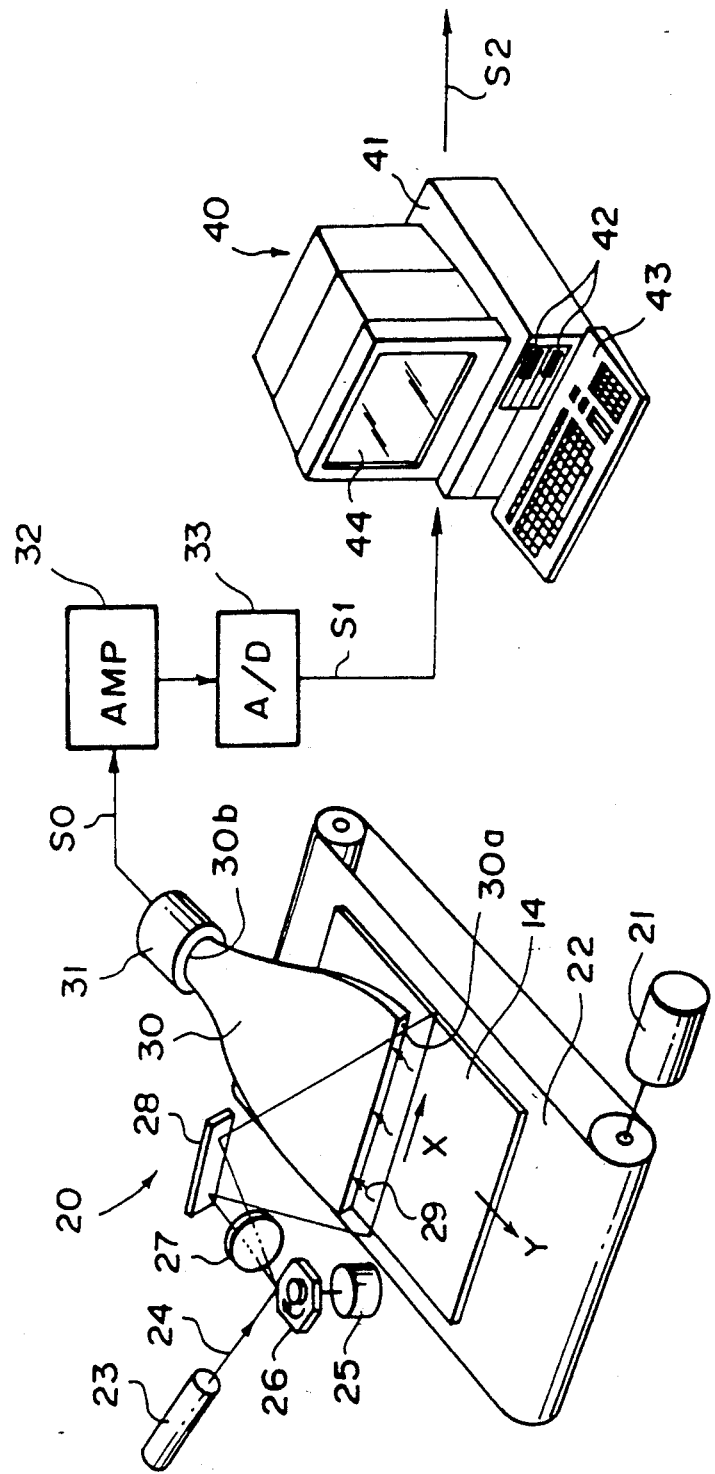
FIG. 4 is a perspective view showing an image processing apparatus in the form of a computer system in accordance with an embodiment of the present invention together with an example of an X-ray image read-out apparatus.

The stimulable phosphor sheet 14 on which an X-ray image has been stored is sent to an X-ray image read-out apparatus 20 as shown in FIG. 4. The stimulable phosphor sheet 14 is conveyed in a sub-scanning direction indicated by the arrow Y by a sheet conveyance means 22 constituted of an endless belt or the like operated by a motor 21. On the other hand, a light beam 24 produced by a laser beam source 23 is reflected and deflected by a rotating polygon mirror 26, which is quickly rotated by a motor 25 in the direction indicated by the arrow, and the light beam 24 passes through a converging lens 27 constituted of an fθ lens or the like. The direction of the optical path of the light beam 24 is then changed by a mirror 28, and the light beam 24 impinges upon the stimulable phosphor sheet 14 and scans across it in a main scanning direction indicated by the arrow X, which main scanning direction is approximately normal to the sub-scanning direction indicated by the arrow Y. When the stimulable phosphor sheet 14 is exposed to the light beam 24, the exposed portion of the stimulable phosphor sheet 14 emits light 29 with an intensity proportional to the amount of energy stored during exposure to X-rays. The emitted light 29 is guided by a light guide member 30, and photoelectrically detected by a photomultiplier 31 which acts as a photodetector. The light guide member 30 is made of a light guiding material such as an acrylic plate, and has a linear light input face 30a positioned so that it extends along the main scanning line on the stimulable phosphor sheet 14, and a ring-shaped light output face 30b is positioned in close contact with a light receiving face of the photomultiplier 31. The emitted light 29 entering the light guide member 30 through its light input face 30a is guided through repeated total reflection inside of the light guide member 30, emanates from the light output face 30b, and is received by the photomultiplier 31. In this manner, the intensity of the emitted light 29, which carries the information about the X-ray image, is converted into an electrical signal by the photomultiplier 31.

The analog output signal SO output from the photomultiplier 31 is amplified by a logarithmic amplifier 32 and is digitized by an A/D converter 33, whereby an image data S1 in the form of a digital signal is obtained.

The image data S1 thus obtained is input into a computer system 40. The computer system includes therein an image processing apparatus in accordance with an embodiment of the present invention, and comprises a main portion 41 in which a CPU and a built-in memory are housed, a disk drive portion 42 which drives floppy disks as an auxiliary memory, a keyboard 43 for manually inputting instructions and the like, and a CRT display 44 for displaying a visible image and other necessary information. The computer system 40 executes the processings described above in conjunction with FIGS. 1 and 2.

Figure 1:
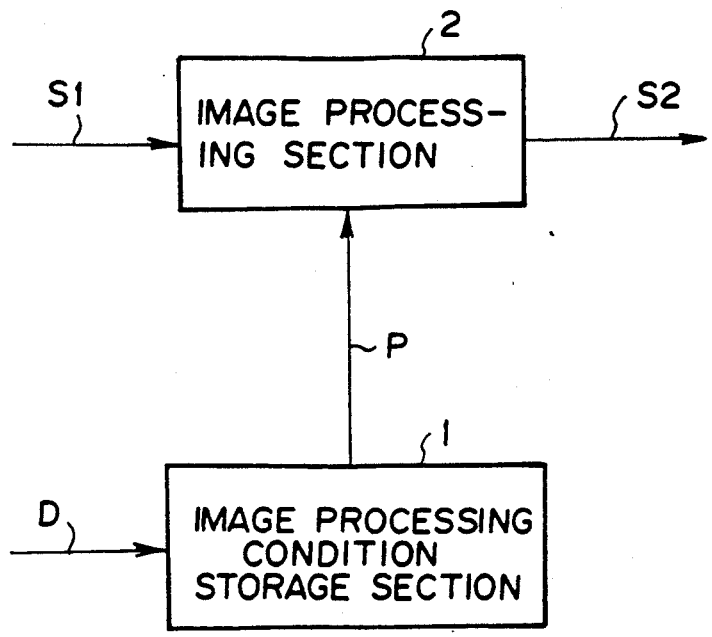
FIG. 1 is a block diagram for illustrating the general arrangement of the image processing apparatus in accordance with the present invention.

First the operation of the computer system 40 when it functions as an example of the image processing apparatus shown in FIG. 1 will be described, hereinbelow.

Image processing conditions which depend upon the recording condition and the recorded part and image processing conditions which depend upon the kind of disease to be diagnosed have been input into the computer system and stored therein.

The computer system 40 executes noise elimination processing for suppressing noise due to fluctuation of X-rays during recording, frequency processing for enhancing or weakening a particular spatial frequency component, processing for changing the gradation, brightness and the like of the visible image displayed by the CRT display 44, and other processings. The image processing condition includes a series of conditions relating to processing of images such as what spatial frequency is to be enhanced to what extent, and what degree the gradation is to be.

When the image data S1 is input into the computer system 40, the image data S1 is processed according to the image processing condition determined based on the recording condition and the recorded part irrespective of the kind of the disease to be diagnosed. The processed image data is sent to the CRT display 44 and is used to reproduce a visible image on the CRT display 44, which is submitted to doctor's inspection. Since the visible image is based on the image data processed according to the image processing condition which has been determined only based on the recording condition and the recorded part, it cannot be always suitable for diagnosis of the disease to be diagnosed. Then the doctor visually inspects the visible image and refers to the patient information such as the result of various tests and doctor's questions, and then inputs the name of disease to be diagnosed by means of the keyboard 43. Thus the name of disease to be diagnosed is delivered to the computer system 40, and the computer system 40 carries out image processing on the image data S1 according to the image processing condition determined based on the name of disease thus delivered to the computer system 40. Then the processed image data is used to reproduce a visible image on the CRT display 44. If desired, the name of disease to be diagnosed may be determined solely based on the patient information such as the result of various tests and doctor's questions without processing the image data S1 according to the image processing condition determined based on the recording condition and the recorded part.

Next the operation of the computer system 40 when it functions as an example of the image processing apparatus shown in FIG. 2 will be described, hereinbelow. For the purpose of simplicity of explanation, it is assumed that the computer system 40 has the sections 1 to 4 shown in FIG. 2, hereinbelow.

The image data S1 is input into the computer system 40 together with the patient information I corresponding to the image data S1. The patient information I is stored in a floppy disk after completing various tests and doctor's questions, and is input into the computer system 40 by loading floppy disk into the disk drive portion 42. The patient information I may be directly input into the computer system 40 without using a floppy disk.

Figure 5:
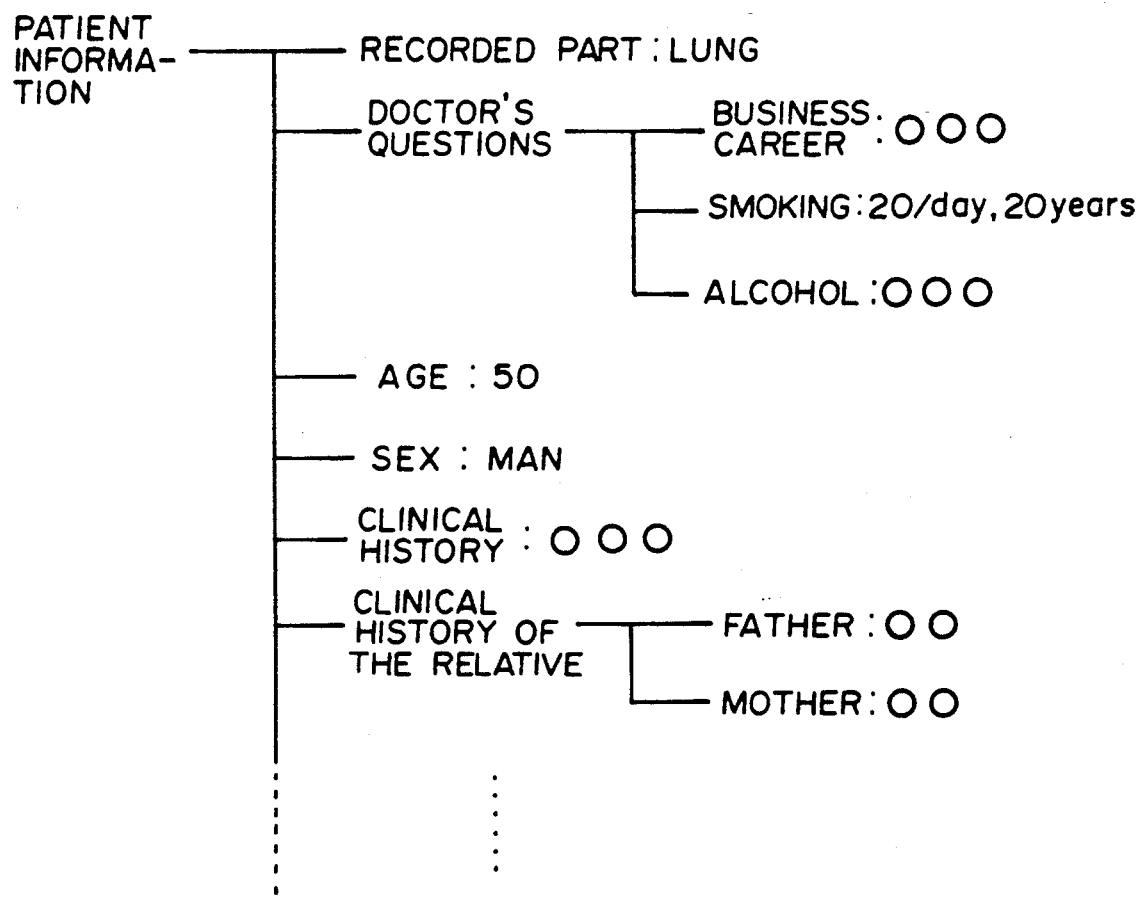
FIG. 5 is a view showing an example of the patient information.

FIG. 5 shows an example of the patient information I. In this particular example, the patient information I includes the recorded part, the result of doctor's questions, age of the patient, sex of the patient, patient's own clinical history, clinical history of patient's relatives and the like and is recorded in a floppy disk in the form of coded data. The patient information is input into the computer system 40 by loading the floppy disk into the computer system 40.

In the image processing condition storage section 1 in the computer system 40 is stored a table in which the names of diseases are related to image processing conditions.

In the diagnosis knowledge base storage section 4 are stored various diagnosis knowledge bases for determining highly probable disease or diseases on the basis of the patient information I. The data analyzing section 3 determines highly probable disease or diseases on the basis of the patient information I according to the diagnosis knowledge bases.

Figure 6A:
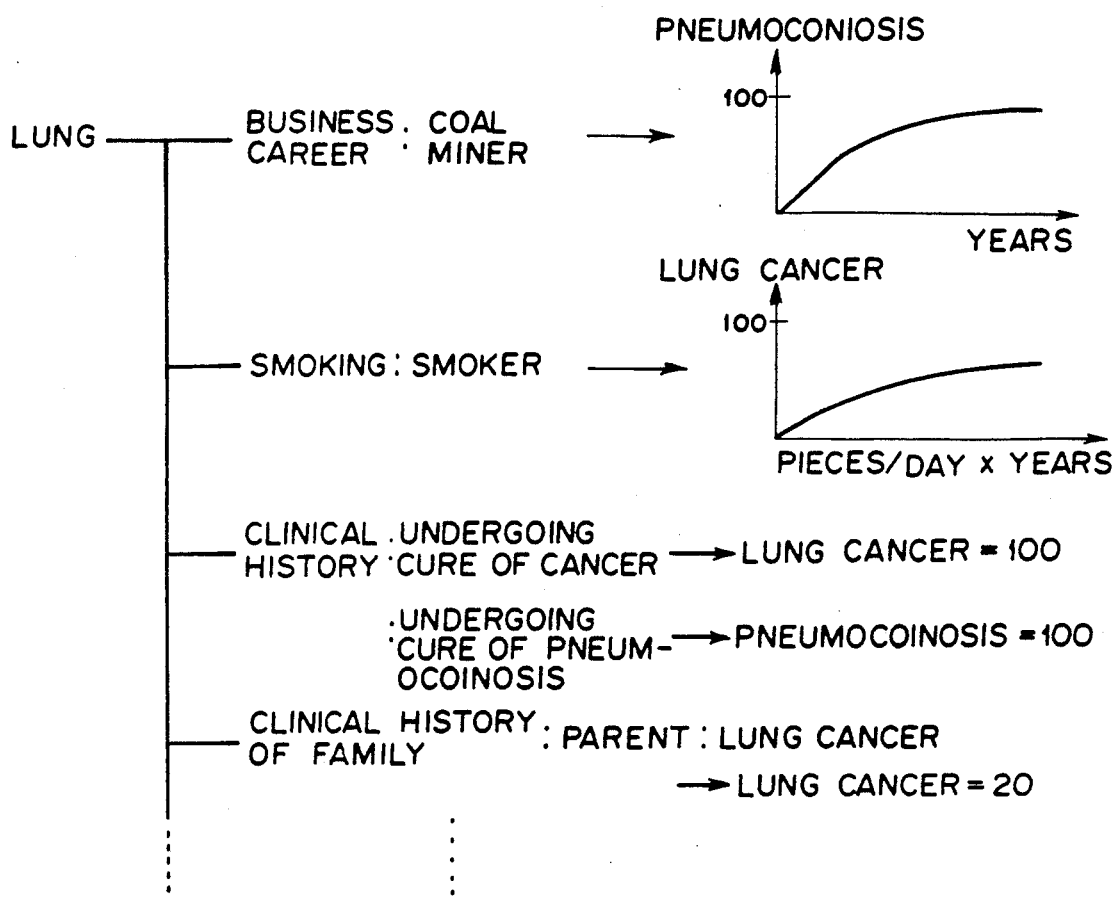
FIGS. 6a and 6b are views showing different examples of the diagnosis knowledge base.
Figure 6B:
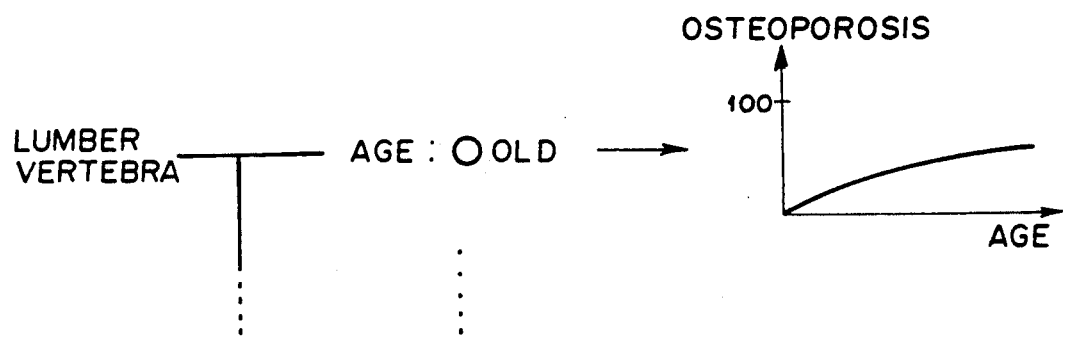

FIGS. 6a and 6b show examples of the diagnosis knowledge bases.

In this particular example, the diagnosis knowledge bases are grouped by the recorded parts such as the lung, the lumber vertebra and the like. For example, when the patient information I input says that the recorded part is the lung, the diagnosis knowledge base on the lung such as shown in FIG. 6a is referred to.

The diagnosis knowledge base on the lung includes the probability of pneumoconiosis as a function of the number of years for which the patient has been working as a coal miner. For example, when the patient information says that the patient has been working as a coal miner for ten years, the data analyzing section 3 determines according to the function that the probability of pneumoconiosis is 30%.

Further the diagnosis knowledge base on the lung includes the probability of lung cancer as a function of the product of the number of cigarettes which the patient smokes a day and the number of years for which the patient has smoked (the total number of cigarettes the patient smoked up to now). For example, when the patient information says that the patient has smoked twenty cigarettes a day for fifteen years, the data analyzing section 3 determines according to the function that the probability of lung cancer is 20%.

When the patient undergoes cure of a certain disease, the probability of the disease is determined to be 100%. Further the probability of disease is also derived from the clinical history of patient's relatives.

The name of disease D thus obtained is input into the image processing condition storage section 1 and the image processing condition storage section 1 inputs the image processing condition P corresponding to the disease into the image processing section 2.

Figure 2:
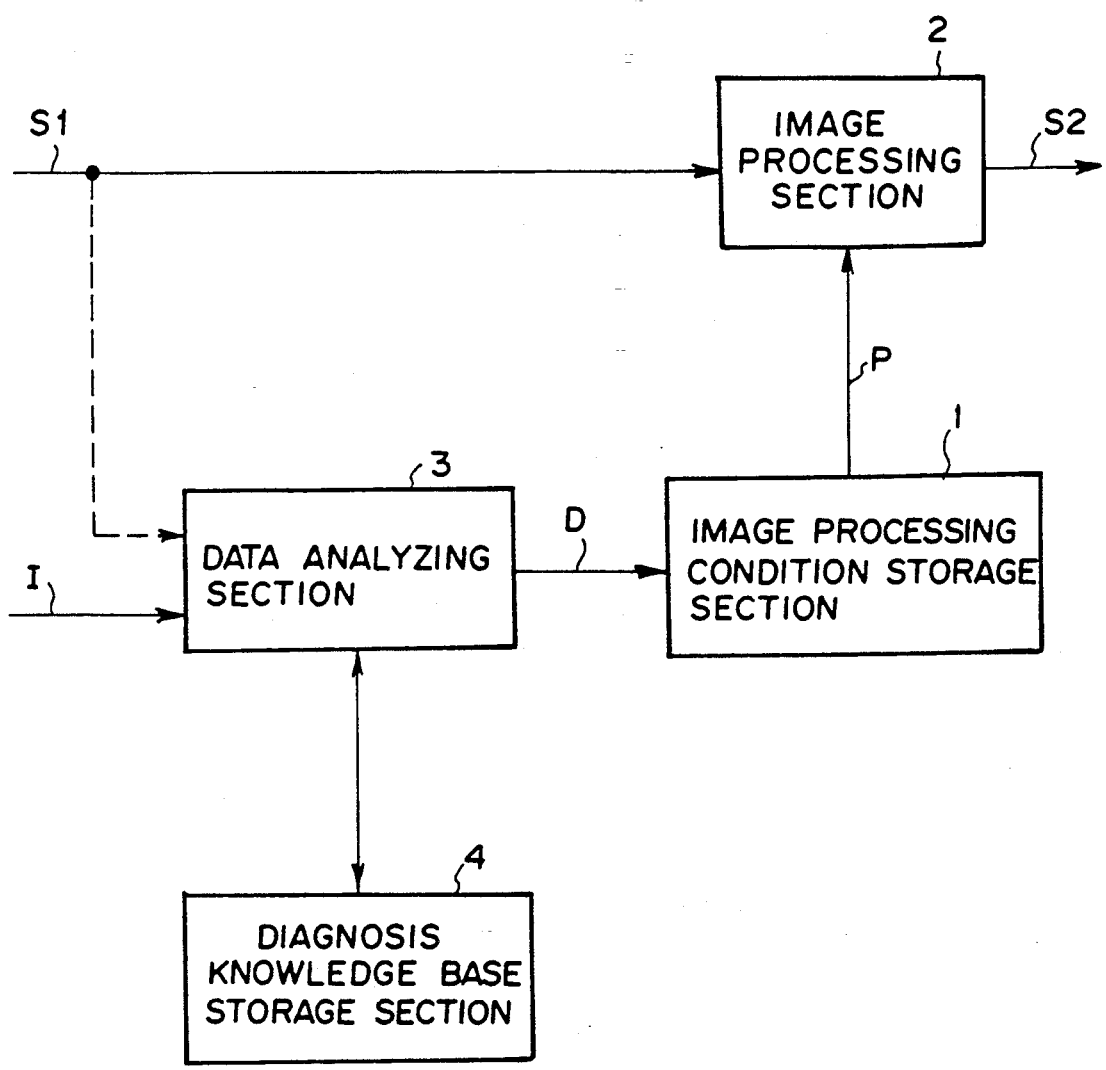
FIG. 2 is a block diagram for illustrating a preferable arrangement of the image processing apparatus in accordance with the present invention.

As shown by the broken line in FIG. 2, the computer system 40 may be so arranged that the image data S1 is input into the data analyzing section 3 together with the patient information I, the image data S1 is searched for an image corresponding to cancer, an image corresponding to pneumoconiosis, or the like and the name of disease corresponding to the image of abnormality, if found, is delivered to the image processing condition storage section 1.

When the name of disease is thus specified, the image data S1 is processed according to the image processing condition corresponding to the disease, and the processed image data S2 is delivered to the CRT display 44 and is used to reproduce a visible image. The processed image data S2 may be stored in a memory (not shown).

More than one disease may be specified. In this case, the image data S1 is processed for each disease and a plurality of visible images may be displayed at one time or in sequence.

In the embodiments described above, the visible image is displayed on the CRT display 44. However the visible image may be recorded on a photosensitive film by means of a laser printer or the like.

Although, in the embodiment described above, the image data is obtained from a system in which the stimulable phosphor sheet is employed as a recording medium, the image processing apparatus of the present invention may be applied to diagnostic images obtained by the use of other various systems such as those obtained by the use of an X-ray film, CT, MRI and the like.

We claim:

1. An image processing apparatus for processing image data corresponding to a diagnostic image from which a disease is to be diagnosed, comprising:

an image processing condition storage section in which image processing conditions specifying the type of image processing for various diseases to be diagnosed are stored; and an image processing section in which the image data is input and the image processing condition corresponding to the disease to be diagnosed through the diagnostic image is input from the image processing condition storage section, and which performs the type of image processing specified by the image processing condition received by the image processing section.

2. An image processing apparatus for processing image data corresponding to a diagnostic image from which a disease is to be diagnosed, comprising:

an image processing condition storage section in which image processing conditions specifying the type of image processing for various diseases to be diagnosed are stored;

a diagnostic knowledge base storage section in which a diagnostic knowledge base for relating patient information corresponding to the diagnostic image to the probability of various diseases to be diagnosed;

a data analyzing section in which the patient information is input and at least one probable disease is specified with reference to the diagnosis knowledge base stored in the diagnosis knowledge base storage section, and an image processing section in which the image data is input and the image processing condition corresponding to the disease specified in the data analyzing section on the basis of the patient information is input from the image processing condition storage section, and which performs the type of image processing the image processing condition input thereinto.

3. An image processing apparatus as defined in claim 2, wherein the image data is input into the data analyzing section together with the patient information, wherein the image data is searched for an image of abnormality which is useful for specifying the disease to be diagnosed, and wherein the name of disease corresponding to the image of abnormality, if found, is delivered to the image processing condition storage section.

4. An image processing apparatus as defined in claim 3 wherein the data analyzing section specifies a plurality of probable diseases with reference to the diagnosis knowledge base stored in the image processing condition storage section and outputs a plurality of image processing conditions corresponding to the respective diseases, and wherein the image processing section carries out image processing on the image data a plurality of times according to the respective image processing conditions.

* * * * *